(12) United States Patent
Skup et al.

(10) Patent No.: US 12,176,100 B2
(45) Date of Patent: Dec. 24, 2024

(54) SYSTEM AND METHOD FOR IMPLANTABLE MEDICAL DEVICE REMOTE PROGRAMMING

(71) Applicant: Pacesetter, Inc., Sylmar, CA (US)

(72) Inventors: Simon Skup, Santa Clarita, CA (US); Mostafa Sadeghi, Los Angeles, CA (US); Eraj D. Kaluarachchi, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 79 days.

(21) Appl. No.: 17/805,823

(22) Filed: Jun. 7, 2022

(65) Prior Publication Data
US 2023/0054317 A1 Feb. 23, 2023

Related U.S. Application Data (60) Provisional application No. 63/235,959, filed on Aug. 23, 2021.

(51) Int. Cl.
*H04L 9/28* (2006.01)
*G06F 8/65* (2018.01)
(Continued)

(52) U.S. Cl.
CPC .............. *G16H 40/40* (2018.01); *G06F 8/65* (2013.01); *H04L 9/3247* (2013.01);
(Continued)

(58) Field of Classification Search
CPC ........ G16H 40/40; G16H 40/67; G16H 80/00; G16H 20/30; G06F 8/65; G06F 21/34;
(Continued)

(56) References Cited

U.S. PATENT DOCUMENTS 5,720,770 A 2/1998 Nappholz et al.
5,752,976 A 5/1998 Duffin et al.
(Continued)

FOREIGN PATENT DOCUMENTS

CN 110418338 11/2019
EP 1478432 B1 7/2009
(Continued)

OTHER PUBLICATIONS

Guanglou Zheng et al., Encryption for Implantable Medical Devices Using Modified One-Time Pads, Jun. 15, 2015, [Retrieved on Jul. 10, 2024]. Retrieved from the internet: <URL: https://ieeexplore.ieee.org/stamp/stamp.jsp?tp=&arnumber=7123574> 12 Pages (825-836) (Year: 2015).*
(Continued)

*Primary Examiner* — Anibal Rivera
(74) *Attorney, Agent, or Firm* — Dean D. Small; The Small Patent Law Group, LLC (57) ABSTRACT

Computer-implemented methods and systems are provided that receive, at an implantable medical device (IMD), a programming package comprising a collection of configuration change requests, transaction credentials, and a signature indicative of a source of the programming package. The transaction credentials include a first hash of the collection of configuration change requests. The IMD validates an external device as the source by decrypting the signature using a key that is uniquely associated with the external device. The IMD verifies the transaction credentials and the configuration change requests of the programming package, and generates a second hash of the collection of configuration change requests. Responsive to both (i) the second hash matching the first hash and (ii) the transaction credentials and the configuration change requests being verified, the
(Continued)

IMD executes the collection of configuration change requests to update an operating configuration of the IMD.

20 Claims, 5 Drawing Sheets

(51) Int. Cl.
| | |
|---|---|
| *G16H 10/60* | (2018.01) |
| *G16H 40/40* | (2018.01) |
| *H04L 9/06* | (2006.01) |
| *H04L 9/08* | (2006.01) |
| *H04L 9/32* | (2006.01) |
| *A61N 1/372* | (2006.01) |
| *G06F 21/34* | (2013.01) |
| *G16H 20/30* | (2018.01) |
| *G16H 40/67* | (2018.01) |
| *H04L 9/30* | (2006.01) |

(52) U.S. Cl.
CPC ...... *A61N 1/37247* (2013.01); *A61N 1/37252* (2013.01); *G06F 21/34* (2013.01); *G16H 20/30* (2018.01); *G16H 40/67* (2018.01); *H04L 9/0631* (2013.01); *H04L 9/0643* (2013.01); *H04L 9/0825* (2013.01); *H04L 9/302* (2013.01)

(58) Field of Classification Search
CPC ... H04L 9/3247; H04L 9/0631; H04L 9/0643; H04L 9/0825; H04L 9/302; H04L 9/6268; A61N 1/37247; A61N 1/37252
See application file for complete search history.

(56) References Cited

U.S. PATENT DOCUMENTS

| | | | |
|---|---|---|---|
| 6,480,745 B2 | 11/2002 | Nelson et al. | |
| 6,622,045 B2 | 9/2003 | Snell et al. | |
| 6,878,112 B2 | 4/2005 | Linberg et al. | |
| 7,039,810 B1 * | 5/2006 | Nichols | G16H 40/40 713/193 |
| 7,060,031 B2 | 6/2006 | Webb et al. | |
| 7,181,286 B2 | 2/2007 | Sieracki et al. | |
| 7,460,910 B2 | 12/2008 | Webb | |
| 7,565,197 B2 | 7/2009 | Haubrich et al. | |
| 7,697,994 B2 | 4/2010 | VanDanacker et al. | |
| 7,983,753 B2 | 7/2011 | Severin | |
| 8,005,546 B1 | 8/2011 | Levine | |
| 8,068,917 B2 | 11/2011 | Petersen et al. | |
| 8,073,542 B2 | 12/2011 | Doerr | |
| 8,239,025 B2 | 8/2012 | Reinke | |
| 8,265,757 B2 | 9/2012 | Mass et al. | |
| 8,352,039 B2 | 1/2013 | Davis et al. | |
| 8,417,339 B2 | 4/2013 | Doerr et al. | |
| 8,423,149 B2 | 4/2013 | Hennig | |
| 8,615,299 B2 | 12/2013 | Goetz | |
| 8,655,447 B2 | 2/2014 | Kukla et al. | |
| 8,694,115 B2 | 4/2014 | Goetz | |
| 8,725,269 B2 | 5/2014 | Nolan et al. | |
| 8,798,760 B2 | 8/2014 | Hoyme et al. | |
| 8,818,522 B2 | 8/2014 | Mass et al. | |
| 8,855,781 B2 | 10/2014 | Doerr | |
| 8,977,360 B2 | 3/2015 | Kim et al. | |
| 9,348,974 B2 | 5/2016 | Goetz | |
| 9,436,481 B2 | 9/2016 | Drew | |
| 9,480,846 B2 | 11/2016 | Strother et al. | |
| 9,713,724 B2 | 7/2017 | Petersen et al. | |
| 9,747,431 B2 | 8/2017 | Chow | |
| 9,979,810 B2 | 5/2018 | Mazar | |
| 9,980,140 B1 | 5/2018 | Spencer et al. | |
| 10,007,473 B2 | 6/2018 | Hampapuram et al. | |
| 10,029,106 B2 | 7/2018 | Gupta et al. | |
| 10,055,550 B2 | 8/2018 | Goetz | |
| 10,124,177 B2 | 11/2018 | Kumar | |
| 10,307,600 B2 | 6/2019 | Ney et al. | |
| 10,322,287 B2 | 6/2019 | Strother et al. | |
| 10,432,403 B2 | 10/2019 | Moskal | |
| 10,549,105 B2 | 2/2020 | Klimovitch et al. | |
| 10,554,632 B2 | 2/2020 | Lange | |
| 10,682,517 B2 | 6/2020 | Hoffman et al. | |
| 10,806,344 B2 | 10/2020 | Goetz | |
| 10,819,713 B2 | 10/2020 | Marnfeldt | |
| 11,154,717 B2 | 10/2021 | Giftakis et al. | |
| 11,164,674 B2 | 11/2021 | Lange | |
| 11,582,022 B1 * | 2/2023 | Creek | H04L 9/0637 |
| 11,628,306 B2 | 4/2023 | St. Martin et al. | |
| 11,904,173 B2 | 2/2024 | Yoder et al. | |
| 11,918,819 B2 | 3/2024 | Eisele et al. | |
| 11,930,126 B2 | 3/2024 | Poltorak | |
| 2005/0049656 A1 | 3/2005 | Petersen et al. | |
| 2006/0074462 A1 | 4/2006 | Verhoef | |
| 2006/0074465 A1 | 4/2006 | Webb | |
| 2006/0161214 A1 | 7/2006 | Patel | |
| 2006/0189854 A1 | 8/2006 | Webb | |
| 2009/0054948 A1 | 2/2009 | Webb | |
| 2009/0112289 A1 | 4/2009 | Lee et al. | |
| 2010/0125174 A1 | 5/2010 | Bevan et al. | |
| 2010/0228314 A1 | 9/2010 | Goetz | |
| 2010/0228322 A1 | 9/2010 | Nolan et al. | |
| 2011/0015693 A1 | 1/2011 | Williamson | |
| 2011/0037614 A1 | 2/2011 | Verhoef | |
| 2011/0172737 A1 | 7/2011 | Davis et al. | |
| 2011/0191828 A1 | 8/2011 | Gould et al. | |
| 2011/0257700 A1 | 10/2011 | Levine | |
| 2012/0035686 A1 | 2/2012 | Petersen et al. | |
| 2012/0197353 A1 | 8/2012 | Donnelly et al. | |
| 2013/0283030 A1 | 10/2013 | Drew | |
| 2014/0107567 A1 | 4/2014 | Geotz | |
| 2016/0253471 A1 | 9/2016 | Volpe | |
| 2016/0330573 A1 * | 11/2016 | Masoud | H04W 12/0431 |
| 2016/0342762 A1 | 11/2016 | Goetz | |
| 2017/0050035 A1 | 2/2017 | Gupta et al. | |
| 2017/0120062 A1 | 5/2017 | Kumar | |
| 2017/0143983 A1 | 5/2017 | Strother et al. | |
| 2018/0309766 A1 | 10/2018 | Marnfeldt | |
| 2019/0036886 A1 | 1/2019 | Wu et al. | |
| 2019/0312734 A1 | 10/2019 | Wentz et al. | |
| 2020/0162437 A1 | 5/2020 | Lange | |
| 2020/0313872 A1 * | 10/2020 | Mondello | H04W 12/033 |
| 2020/0398062 A1 * | 12/2020 | Ibarrola | A61N 1/37254 |
| 2021/0000349 A1 | 1/2021 | Goetz | |
| 2021/0035674 A1 | 2/2021 | Volosin et al. | |
| 2021/0058257 A1 * | 2/2021 | Pepin | H04L 9/3247 |
| 2021/0064605 A1 * | 3/2021 | Bálint | H04W 12/35 |
| 2021/0085861 A1 * | 3/2021 | Patel | G16H 40/60 |
| 2021/0213294 A1 | 7/2021 | Crawford | |
| 2021/0236830 A1 | 8/2021 | Tahmasian | |
| 2021/0268296 A1 | 9/2021 | Flakne et al. | |
| 2021/0343017 A1 | 11/2021 | Jordan | |
| 2022/0096847 A1 | 3/2022 | Shah et al. | |
| 2022/0141663 A1 | 5/2022 | Kothandaraman et al. | |
| 2023/0100246 A1 * | 3/2023 | DeBates | H04N 7/14 705/2 |
| 2023/0108034 A1 | 4/2023 | Fischer et al. | |

FOREIGN PATENT DOCUMENTS

| | | |
|---|---|---|
| EP | 3171930 A1 | 5/2017 |
| EP | 3615136 B1 | 6/2021 |

OTHER PUBLICATIONS

Extended European Search Report for related European Patent Application No. 22176538.1 dated Nov. 3, 2022 (8 pages).

Chenglong et al, "POKs Based Secure and Energy-Efficient Access Control for Implantable Medical Devices", arxiv.org, Cornell University Library, 201 Olin Library Cornell University Ithaca, NY 14853, Mar. 27, 2018 (20 pages).

Ellouze Nourhene et al: "Powerless security for Cardiac Implantable Medical Devices: Use of Wireless Identification and Sensing (56) References Cited

OTHER PUBLICATIONS

Platform", Journal of Network and Computer Applications, Academic Press, New York, NY, US, vol. 107, Feb. 2, 2018 (21 pages).

* cited by examiner

SYSTEM AND METHOD FOR IMPLANTABLE MEDICAL DEVICE REMOTE PROGRAMMING

CROSS-REFERENCE TO RELATED APPLICATIONS

This application claims priority to U.S. Provisional Patent Application No. 63/235,959, filed Aug. 23, 2021 and titled System And Method For Implantable Medical Device Remote Programming. The subject matter of the provisional application is incorporated herein by reference in its entirety.

BACKGROUND

Embodiments of the present disclosure generally relate to methods, systems, and devices for updating operating configurations of implantable medical devices (IMDs) via remote communications.

An implantable medical device (IMD) is a medical device that is configured to be implanted within a patient anatomy and commonly employs one or more electrodes that either receive or deliver voltage, current or other electromagnetic pulses from or to an organ or tissue for diagnostic or therapeutic purposes. In general, IMDs include a battery, electronic circuitry, a pulse generator, a transceiver, and a microprocessor. The microprocessor is configured to handle communication with an external device or instrument as well as control patient therapy. The components of the IMD are hermetically sealed within a housing. The IMD is completely enclosed within the human body. Thus, there is no means of direct interaction between an IMD and an external device, other than through wireless communication.

The IMD may require programming updates over time to adjust the behavior and operations of the IMD. The programming updates are wirelessly communicated from an external device outside of the patient to the IMD within the patient. The programming communications need to be secure to ensure the authenticity and integrity of the exchanged information. One way to authenticate wireless programing communications is to enable the IMD to detect proximity to the external device transmitting the programming update, and another way is to enable the IMD to connect to a network (e.g., the Internet) for communicating with a certificate authority. However, each of these approaches requires additional hardware and software (e.g., proximity sensor, network connectivity, etc.) that would add cost, would occupy valuable space in the housing of the IMD, and would draw significant power from the onboard battery of the IMD, which is typically non-rechargeable.

A need remains for improved methods and systems for establishing secure remote programming communications between IMDs and external devices utilizing existing hardware and without unduly drawing power from the battery.

SUMMARY

In accordance with an embodiment, an IMD is provided that includes a housing configured to be implanted within a patient and one or more processors disposed within the housing. The one or more processors are configured to receive a programming package comprising a collection of configuration change requests, transaction credentials, and a signature indicative of a source of the programming package. The transaction credentials include a first hash of the collection of configuration change requests. The one or more processors are configured to validate an external device as the source by decrypting the signature using a key that is uniquely associated with the external device; verify the transaction credentials and the configuration change requests of the programming package; and generate a second hash of the collection of configuration change requests. Responsive to both (i) the second hash matching the first hash and (ii) the transaction credentials and the configuration change requests being verified, the one or more processors are configured to execute the collection of configuration change requests to update an operating configuration of the IMD.

Optionally, responsive to at least one of (i) the second hash not matching the first hash or (ii) at least one of the transaction credentials or the configuration change requests is not verified, the one or more processors are configured to forgo execution of the collection of configuration change requests. Optionally, the transaction credentials comprise an expiration credential that includes a designated time that the programming package expires. The one or more processors are configured to verify the expiration credential of the transaction credentials by determining that the programming package is not expired.

Optionally, the transaction credentials comprise a target device credential that identifies one or both of a particular device or a device platform intended to execute the collection of configuration change requests. The one or more processors are configured to verify the target device credential by determining that the IMD is the particular device or has the device platform. Optionally, the transaction credentials comprise a role credential that provides a privilege level of a user that selected the collection of configuration change requests. The one or more processors are configured to verify each of the configuration change requests by determining that each respective configuration change request does not exceed the privilege level associated with the role credential. Optionally, the transaction credentials comprise a programming credential that identifies one or both of a current operating configuration of the IMD or a last programming timestamp indicating a most recent update of the operating configuration of the IMD. The one or more processors are configured to verify the programming credential by confirming that the programming credential is correct.

Optionally, responsive to execution of the collection of configuration change requests, the one or more processors are configured to generate a result message for communication to the external device. The result message indicates that the operating configuration of the IMD is updated. Optionally, the key is a public key that is stored within a memory device of the IMD. The signature in the programming package is generated by the external device using a private key that is uniquely associated with the external device and forms a key pair with the public key.

Optionally, the IMD has a communication modem that is configured to wirelessly receive the programming package while the IMD is subcutaneously disposed within the patient. Optionally, the one or more processors are configured to validate the external device as the source of the programming package by determining that decrypted data of the signature matches one or more of the transaction credentials of the programming package. Optionally, the one or more processors are configured to generate the second hash based on an order at which the configuration change requests of the programming package are received by the IMD.

In at least one embodiment, a system is provided that includes an IMD and one or more external devices. The IMD includes a housing configured to be implanted within a patient and one or more processors disposed within the housing. Each of the one or more external devices includes a controller and a communication circuit. The controller of at least one of the one or more external devices is configured to obtain a collection of configuration change requests; obtain a set of transaction credentials; and generate a first hash of the collection of configuration change requests. The first hash represents one of the transaction credentials in the set. The controller is also configured to generate a signature by encrypting one or more of the transaction credentials in the set using a first key that is uniquely associated with a first external device of the one or more external devices, and build a programming package by combining the collection of configuration change requests, the set of transaction credentials, and the signature. The communication circuit of at least one of the one or more external devices is configured to wirelessly communicate the programming package to the IMD. The one or more processors of the IMD are configured to receive the programming package from the communication circuit of the one or more external devices, and validate the first external device as a source of the programming package by decrypting the signature using either the first key or a second key that is uniquely associated with the first external device. The first key or the second key used to decrypt the signature is stored within a memory device of the IMD. The one or more processors of the IMD are configured to verify the transaction credentials and the configuration change requests of the programming package, and generate a second hash of the collection of configuration change requests. Responsive to both (i) the second hash matching the first hash and (ii) the transaction credentials and the configuration change requests being verified, the one or more processors of the IMD are configured to execute the collection of configuration change requests to update an operating configuration of the IMD.

Optionally, the first key is a private key associated with the first external device. The one or more processors of the IMD are configured to use the second key to decrypt the signature. The second key is a public key that forms a key pair with the private key. Optionally, responsive to at least one of (i) the second hash not matching the first hash or (ii) at least one of the transaction credentials or the configuration change requests is not verified, the one or more processors of the IMD are configured to forgo execution of the collection of configuration change requests. Optionally, the one or more external devices include or represent one or more of a clinician programmer device, a bedside monitor, a smartphone, a tablet computer, a laptop computer, a desktop computer, a server, or a wearable computer.

Optionally, the transaction credentials comprise the first hash and at least two of: (i) an expiration credential that includes a designated time that the programming package expires; (ii) a target device credential that identifies one or both of a particular device or a device platform intended to execute the collection of configuration change requests; (iii) a role credential that provides a privilege level of a user that selected the collection of configuration change requests; and (iv) a programming credential that identifies one or both of a current parameter set of the IMD or a last programming timestamp indicating a most recent update of the operating configuration of the IMD. Optionally, the communication circuit of the one or more external devices is configured to wirelessly communicate the programming package to the IMD while the IMD is subcutaneously implanted within the patient and the one or more external devices are outside of the patient.

In at least one embodiment, a method is provided that includes receiving a programming package at an IMD configured to be implanted within a patient. The programming package includes a collection of configuration change requests, transaction credentials, and a signature indicative of a source of the programming package. One of the transaction credentials is a first hash of the collection of configuration change requests. The method includes validating, via one or more processors of the IMD, an external device as the source by decrypting the signature using a key that is uniquely associated with the external device and stored within a memory device of the IMD. The method also includes verifying the transaction credentials and the configuration change requests of the programming package, and generating a second hash of the collection of configuration change requests. Responsive to both (i) the second hash matching the first hash and (ii) the transaction credentials and the configuration change requests being verified, the method includes executing the collection of configuration change requests to update an operating configuration of the IMD.

Optionally, validating the external device as the source of the programming package includes determining that decrypted data of the signature, using the key, matches one or more of the transaction credentials of the programming package. Optionally, responsive to at least one of (i) the second hash not matching the first hash or (ii) at least one of the transaction credentials or the configuration change requests is not verified, the method comprises forgoing execution of the collection of configuration change requests.

DETAILED DESCRIPTION

Embodiments herein provide methods and systems that are designed to enhance integrity and authenticity of wireless programming communications between one or more external devices and an IMD.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

The terms "subdermal" and "subcutaneous" shall mean below the skin, but not intravenous (e.g., non-transvenous). For example, an implant device within a subcutaneous pocket is not located in a chamber of the heart, in a vein on the heart, or in the lateral or posterior branches of the coronary sinus. A subdermal or subcutaneous pocket is located below the skin but above the muscle.

The term "obtains" and "obtaining", as used in connection with data, signals, information and the like, include at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

Figure 1:
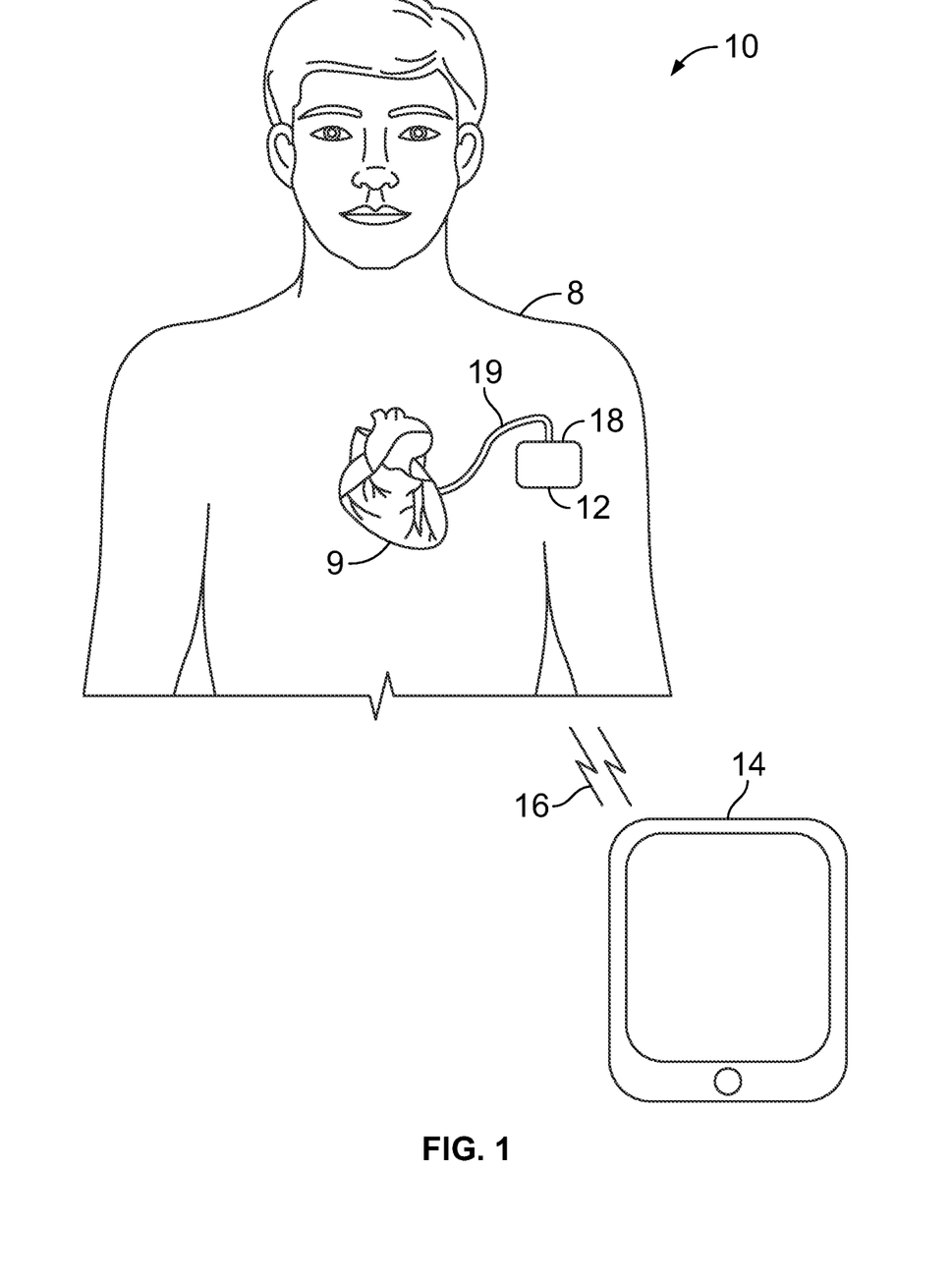
FIG. 1 illustrates a simplified block diagram of a system operated in accordance with embodiments herein.

FIG. 1 illustrates a simplified block diagram of a system 10 operated in accordance with embodiments herein. The system 10 includes an IMD 12 and one or more external devices or instruments 14. A single external device 14 is illustrated in FIG. 1. The IMD 12 and the external device 14 are configured to communicate with one another wirelessly over a wireless communication link 16. In an embodiment, the external device 14 updates an operating configuration of the IMD 12 by transmitting a programming package to the IMD 12 along the communication link 16. The embodiments described herein provide an algorithm or workflow for verifying the validity, integrity, and authenticity of configuration change requests of the programming package prior to executing the configuration change requests to update the operating configuration of the IMD. For example, a configuration change for an implantable pacemaker or cardioverter defibrillator may represent a change in sensitivity threshold, a change in heart rate thresholds for binning atrial fibrillation or tachycardia events, a change in the number of arrhythmia events that should occur before delivering a therapy, a change in communications gain, a change in a communications protocol, or the like. A configuration change may include updates to executing operations of importance for diagnosis and/or clinical care, such as lead impedance testing, testing for level of sensing, or even disabling device operations as part of palliative care.

The IMD 12 is implanted within a patient 8 at a site near the heart 9. The IMD 12 may be a cardiac pacemaker, an implantable cardiac monitoring device (ICM), a defibrillator, an ICM coupled with a pacemaker, or the like. The IMD 12 is intended for implantation within a subcutaneous pocket of the patient. The IMD 12 may be configured to sense cardiac signals to monitor cardiac activity over time. Optionally, the IMD 12 may also be configured to deliver stimulation therapy to the heart 9. For example, the IMD 12 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto.

The IMD 12 in the illustrated embodiment includes a body or housing 18 that is connected to at least one lead 19. A single lead 19 is shown in FIG. 1, but the IMD 12 may include multiple leads in another embodiment. The lead 19 extends from the housing 18 to the heart 9, such that the distal end is in contact with patient tissue surrounding the heart 9. The lead 19 includes one or more electrodes that may measure cardiac signals of the heart 9 and deliver stimulation therapy to the heart 9. In an embodiment, a single electrode may emit a stimulation pulse in a stimulation mode, and then may quickly switch to a monitoring mode to detect cardiac signals following the stimulation pulse.

Although the IMD 12 in the illustrated embodiment includes a lead 19, one or more of the embodiments described herein utilize a leadless IMD that does not include any lead. For example, the IMD 12 may be a leadless pacemaker, a leadless cardiac monitoring device (ICM), or the like. In general, the IMD 12 may represent a cardiac monitoring device, pacemaker, cardioverter, cardiac rhythm management device, defibrillator, neurostimulator, leadless monitoring device, leadless pacemaker, and the like. For example, the IMD may include one or more structural and/or functional aspects of the device(s) described in U.S. Pat. No. 9,333,351 "Neurostimulation Method And System To Treat Apnea"; U.S. Pat. No. 9,044,610 "System And Methods For Providing A Distributed Virtual Stimulation Cathode For Use With An Implantable Neurostimulation System"; U.S. Pat. No. 10,765,860 "Subcutaneous Implantation Medical Device With Multiple Parasternal-Anterior Electrodes"; U.S. Pat. No. 10,722,704 "Implantable Medical Systems And Methods Including Pulse Generators And Leads"; and U.S. Pat. No. 11,045,643 "Single Site Implantation Methods For Medical Devices Having Multiple Leads", which are hereby incorporated by reference in their entireties. Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference. Additionally or alternatively, embodiments may be implemented utilizing all or portions of the methods and systems described in U.S. application Ser. No. 16/930,791, filed Jul. 16, 2020 and titled "METHODS, DEVICES AND SYSTEMS FOR HOLISTIC INTEGRATED HEALTHCARE PATIENT MANAGEMENT" (U.S. Publication No. 2021/0020294).

In another example, the IMD 12 may be an ICM that includes one or more structural and/or functional aspects of the device(s) described in U.S. Pat. No. 9,949,660, entitled, "Method And System To Discriminate Rhythm Patterns In Cardiac Activity," which is expressly incorporated herein by reference. All references, including publications, patent applications and patents, cited herein are hereby incorporated by reference to the same extent as if each reference were individually and specifically indicated to be incorporated by reference and were set forth in its entirety herein.

The housing 18 may contain a battery, pulse generation circuitry, communication circuitry, a data storage device (e.g., memory), and/or control circuitry including one or more processors. The control circuitry is for receiving and analyzing electrocardiogram IEGM signals from the electrodes 13. The control circuitry may include at least one processor for processing the IEGM signals in accordance with algorithms to make determinations about the state of the heart 9. The memory provides storage for the cardiac signals and programmed instructions for the control circuitry. The battery powers the circuitry with the housing 10. For example, the battery powers the pulse generation circuitry to generate stimulation pulses and powers the communication circuitry to communicate with an external device 16. The control circuitry may generate messages to be communicated via the communication circuitry to the external device 14. The messages may include the IEGM signals and/or data generated based on the IEGM signals. The control circuitry is also configured to analyze messages, received via the communication circuit from the external device 14, that include programming packages for updating the operating configuration, including settings, parameters, behavior, and the like, of the IMD 12. Exemplary structure for the IMD 12 is discussed and illustrated below in connection with FIG. 2.

The external device 14 may represent a computing device that is accessible or possessable by the patient or a clinician, such as a tablet computer, a smartphone, a wearable device, laptop computer, a desktop computer, a bedside monitor installed in a patient's home, or the like. The external device 14 alternatively may be a programmer device used in the clinic by a clinician. The external device may be one of the devices listed above that is communicatively connected to a second external device that represents the source of the programming package intended to update the operating configuration of the IMD 12. For example, the second external device may be a server or another computing device that is communicatively connected to the first external device 14 via a network connection (e.g., the Internet). In general, the external device 14 facilitates access by physicians to patient data as well as permits the physician to review real-time electrocardiogram (ECG) signals and, as specifically described herein, update the operating configuration of the IMD 12 without the clinician being near the patient.

Figure 2:
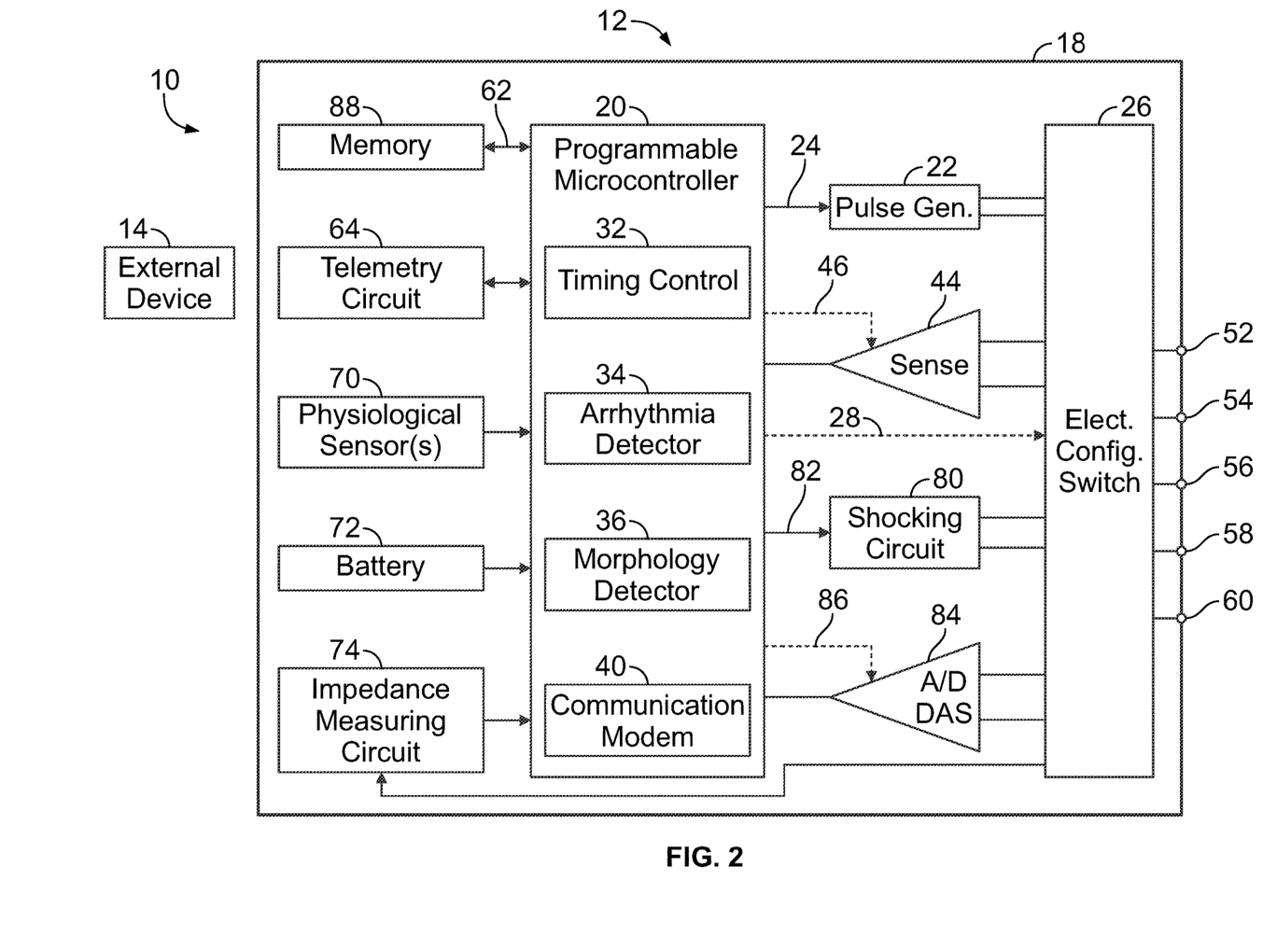
FIG. 2 shows a block diagram of the system of FIG. 1 according to an embodiment.

FIG. 2 shows a block diagram of the system 10 according to an embodiment. The housing 18 or case of the IMD 12 holds the electronic and/or computing components. The housing 18 further includes a connector (not shown) with at least one terminal 52 and optionally additional terminals 54, 56, 58, 60. The terminals may be connected to electrodes that are located in various locations within and about the heart, such as on the lead 19 (shown in FIG. 1). The electrodes may include various combinations of ring, tip, coil, shocking electrodes, and the like.

The IMD 12 includes a programmable microcontroller 20 that controls various operations of the IMD 12, including cardiac monitoring and stimulation therapy. Microcontroller 20 includes a one or more processors (e.g., a microprocessors or equivalent control circuitry), RAM and/or ROM memory, logic and timing circuitry, state machine circuitry, and I/O circuitry. Microcontroller 20 includes an arrhythmia detector 34 that is configured to cardiac activity data to identify potential atrial fibrillation (AF) episodes as well as other arrhythmias (e.g., Tachycardias, Bradycardias, Asystole, etc.).

An electrode configuration switch 26 is optionally provided to allow selection of different electrode configurations under the control of the microcontroller 20. The electrode configuration switch 26 may include multiple switches for connecting the desired electrodes to the appropriate I/O circuits, thereby facilitating electrode programmability. The switch 26 is controlled by a control signal 28 from the microcontroller 20. Optionally, the switch 26 may be omitted and the I/O circuits directly connected to a housing electrode.

The IMD 12 may include a chamber pulse generator 22 that generates stimulation pulses for connecting the desired electrodes to the appropriate I/O circuits, thereby facilitating electrode programmability. The pulse generator 22 is controlled by the microcontroller 20 via control signals 24. The IMD 12 includes a sensing circuit 44 selectively coupled to one or more electrodes that perform sensing operations through the switch 26 to detect cardiac activity. The sensing circuit 44 may include dedicated sense amplifiers, multiplexed amplifiers, or shared amplifiers. The sensing circuit 44 may operate in a unipolar sensing configuration or a bipolar sensing configuration. The output of the sensing circuit 44 is connected to the microcontroller 20 which, in turn, triggers, or inhibits the pulse generator 22 in response to the absence or presence of cardiac activity. The sensing circuit 44 receives a control signal 46 from the microcontroller 20 for purposes of controlling the gain, threshold, polarization, and timing of any blocking circuitry (not shown) coupled to the sensing circuit.

The IMD 12 further includes an analog-to-digital A/D data acquisition system (DAS) 84 coupled to one or more electrodes via the switch 26 to sample cardiac signals across any pair of desired electrodes. The A/D DAS 84 is controlled by a control signal 86 from the microcontroller 20.

The IMD 12 is further equipped with a communication modem (modulator/demodulator) or circuit 40 to enable wireless communication. The modem 240 enables timely and accurate data transfer directly from the patient to the external device 14, and vice-versa. For example, the communication modem 40 is configured to establish the communication link 16 with the external device 14. In an embodiment, the communication modem 40 receives a programming package from the external device 14 and conveys the programming package to the microcontroller 20 for verification prior to executing configuration change requests and/or command execution requests contained within the programming package. In addition to remote programming of the IMD 12, the wireless communication link 16 with the external device 14 facilitates access by physicians and/or patients to patient data generated by the IMD 12.

The communication modem 40 may utilize radio frequency (RF), Bluetooth, or Bluetooth Low Energy telemetry protocols. The signals are transmitted in a high frequency range and will travel through the body tissue in fluids without stimulating the heart or being felt by the patient. The communication modem 40 may be implemented in hardware as part of the microcontroller 20, or as software/firmware instructions programmed into and executed by the microcontroller 20. Alternatively, the modem 40 may reside separately from the microcontroller 20 as a standalone hardware component.

The microcontroller 20 is coupled to a non-transitory data storage device, referred to herein as memory device 88, by a suitable data/address bus 62. The memory device 88 stores programmable operating parameters used by the microcontroller 20 and/or data associated with the detection and determination of arrhythmias. In an embodiment, the memory device 88 also stores one or more keys used to decrypt a cryptographic signature of a received programming package to validate a source of the programming package. For example, the memory device 88 may store a public key that is uniquely associated with the external device 14 or another external device, which generates or builds the programming package.

The IMD 12 optionally includes one or more physiologic sensors 70 that adjust pacing stimulation rates, detect changes in cardiac output, changes in the physiological condition of the heart, and/or diurnal changes in activity (e.g., detecting sleep and wake states). Examples of physiological sensors 70 might include sensors that, for example, sense respiration rate, pH of blood, ventricular gradient, activity, body movement, position/posture, minute ventilation (MV), and/or the like.

The battery 72 provides operating power to all of the components in the IMD 12. The battery 72 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more).

The IMD 12 further includes an impedance measuring circuit 74, which can be used for many things, including sensing respiration phase. The IMD 12 may be further equipped with a telemetry circuit 64 that can selectively communicate with an external device, such as the device 14, when connected via a physical (e.g., wired) communication link. The IMD 12 includes a shocking circuit 80 controlled by control signals 86 generated by the microcontroller 20. The shocking circuit 80 generates shocking pulses of low (e.g., up to 0.5 joules), moderate (e.g., 0.5-10 joules), or high energy (e.g., 11 to 40 joules), as controlled by the microcontroller 20. In an alternative embodiment in which the IMD 12 senses and monitors cardiac activity without administering stimulation therapy, the IMD 12 may lack the pulse generator 22 and the shocking circuit 80.

The microcontroller 20 may include other dedicated circuitry and/or firmware/software components, such as a timing control (module) 32 and a morphology detector (module) 36. The timing control 32 is used to control various timing parameters, such as stimulation pulses (e.g., pacing rate, atria-ventricular (AV) delay, atrial interconduction (A-A) delay, ventricular interconduction (V-V) delay, etc.) as well as to keep track of the timing of RR-intervals, refractory periods, blanking intervals, noise detection windows, evoked response windows, alert intervals, marker channel timing, and the like. The morphology detector 36 is configured to review and analyze one or more features of the morphology of cardiac activity signals, such as the morphology of detected R waves to determine whether to include or exclude one or more beats from further analysis.

Figure 3:
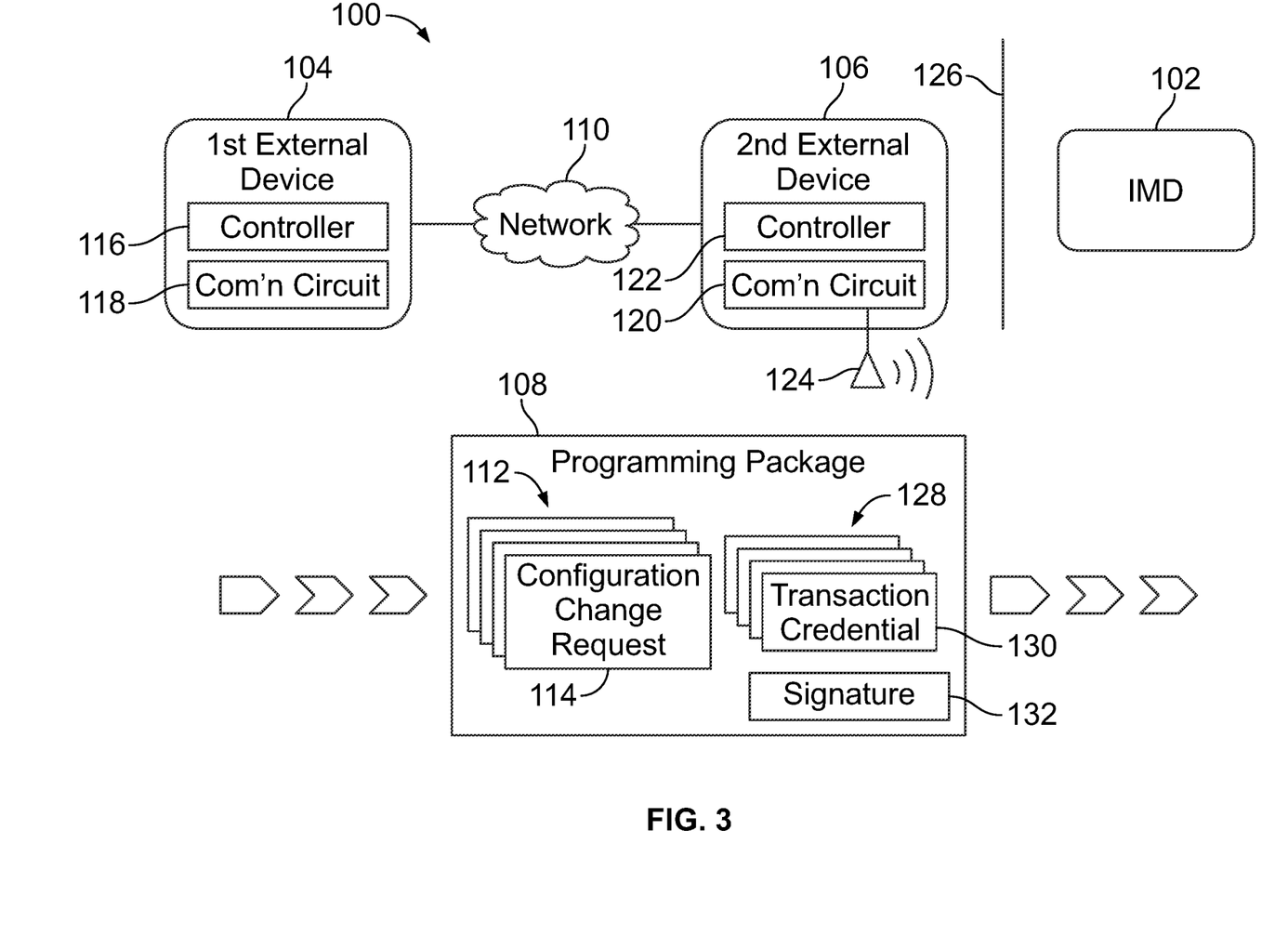
FIG. 3 is a schematic illustration of a system according to an embodiment.

FIG. 3 is a schematic illustration of a system 100 according to an embodiment. The system 100 provides secure remote programming of an IMD 102 while the IMD 102 is implanted within a patient. In addition to the IMD 102, the system 100 includes one or more external devices. In the illustrated embodiment, the external devices include a first external device 104 and a second external device 106, but the system 100 may include only a single external device or more than two external devices in other embodiments. The system 100 may represent the system 10 shown in FIGS. 1 and 2. For example, the IMD 102 may represent the IMD 12 and the second external device 106 may represent the external device 14.

The one or more external devices build a programming package 108 that is designed to update an operating configuration of the IMD 102. The operating configuration of the IMD 102 generally refers to the specific settings, functions, parameters, and the like that dictate the device behavior. For example, the operating configuration affects how the IMD 102 collects data, such as cardiac signals, how the IMD 102 analyzes the data, and how the IMD 102 responds to the data. The response may include activating the pulse generator or shocking circuit to deliver stimulation therapy to the patient, saving data in the memory device, communicating data to the external device 106, or the like. Even if the IMD 102 has been previously programmed, the operating configuration may be updated over time due to physiological changes in the patient, unplanned movement of the IMD 102 within the patient, or even to enhance functionality of the IMD 102 based on software developments.

In the illustrated embodiment, the first external device 104 builds the programming package 108. In a non-limiting example, the first external device 104 is accessed and utilized by a clinician to select a collection 112 of multiple configuration change requests 114 for inclusion in the programming package 108. The first external device 104 may be a clinician programmer device, a workstation, or a computing device (e.g., smartphone, tablet computer, laptop computer, etc.). The clinician may select the collection 112 by communicating via a network 110 with a server or other computing device in the cloud. For example, the clinician may be required log in to a secure portal prior to receiving access to select the configuration change requests 114 and command the generation of the programming package 108.

The first external device 104 may be remote from the second external device 106 and the patient.

The first external device 104 conveys the programming package 108, as a message, to the second external device 106 via the network 110. In a non-limiting example, the second external device 106 is a device that is disposed proximate to the patient, at least at a time that the second external device 106 communicates the programming package 108 to the IMD 102. For example, the second external device 104 may be a bedside monitoring device or a computing device utilized or possessed by the patient, such as a smartphone, tablet computer, laptop computer, or the like.

When the second external device 106 receives the programming package 108, the programming package 108 may schedule a designated time in the future at which to transmit the programming package 108 to the IMD 102. The second external device 106 initially stores the programming package 108 in a memory device of the device 106 until the designated time. At the designated time, the second external device 106 wirelessly transmits the programming package 108 to the IMD 102. This process of scheduling in advance the delivery of the programming package to the IMD via an intermediary device is referred to as asynchronous remote programming. The IMD 102 is implanted within the patient at the time that the IMD 102 receives the programming package 108. According to embodiments herein, the IMD 102 performs a series of operations to verify the authenticity, validity, and integrity of the programming package 108 prior to executing the collection 112 of configuration change requests 114. If all of the elements of the programming package 108 are verified, then the IMD 102 executes all of the configuration change requests 114 to update the operating configuration of the IMD 102. On the other hand, if at least one of the elements are not verified, as described herein, then the IMD 102 does not execute any of the configuration change requests 114, such that the operating configuration of the IMD 102 is not updated.

The first and second external devices 104, 106 include respective controller circuits (e.g., controllers) and communication circuits. Each of the controllers includes one or more processors. In the process described above, the controller 116 of the first external device 104 generates the programming package 108. The communication circuit 118 of the first external device 104 communicates the programming package 108 to the second external device 106 via the network 110. The communication circuit 120 of the second external device 106 receives the programming package 108 and conveys the package 108 to the controller 122 of the second external device 106 for analysis. The controller 122 determines the scheduled delivery time and transmission characteristics, such as frequency channel and protocol, for communicating the programming package 108 to the IMD 102. At the scheduled delivery time, the controller 122 utilizes the communication circuit 120 to transmit the programming package 108 to the IMD 102. The communication circuit 120 may include an antenna 124 that wirelessly transmits the programming package 108 via RF signals, such as Bluetooth. The signals that represent the programming package 108 penetrate the body 126 of the patient and reach a receiver of the IMD 102. The receiver may be the communication modem 40 shown in FIG. 2, which conveys the received data packets to the one or more processors of the microcontroller 20 for analysis. In this way, the IMD 102 is beneficially able to receive the programming package 108 without requiring a network connection or a proximity sensor.

In instances as described above in which the communication of the programming package 108 from the source to the IMD 102 is delayed and/or indirect, there is a risk that the contents of the programming package 108 may be tampered with or corrupted after generation and before receipt by the IMD 102. The system 100 and method described herein perform cryptographic operations to ensure that the configuration change requests 114 are immutable and that the source of the package 108 is authenticated prior to execution by the IMD 102.

Figure 4:
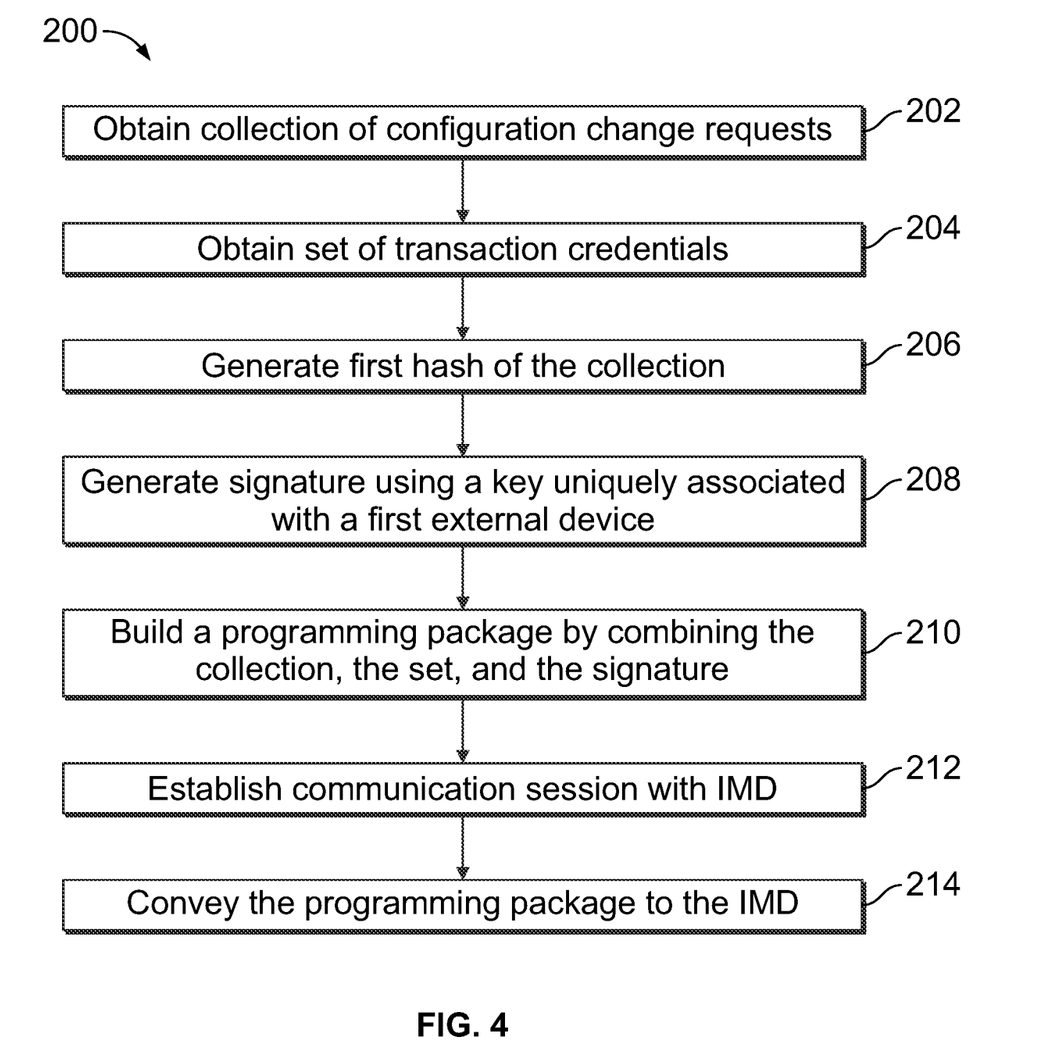
FIG. 4 is a flow chart of a method for providing a programming package to an IMD.

FIG. 4 is a flow chart of a method 200 for providing a programming package to an IMD. The method 200 shown in FIG. 4 may represent a portion of a larger method for providing secure, remote programming of an IMD. The method 200 is performed by one or more external devices. The method 200 in FIG. 4 is described with reference to FIG. 3, so the following operations may be performed by one or both of the external devices 104, 106.

At step 202, a collection 112 of multiple configuration change requests 114 are obtained. The external device, or one or more processors (e.g., controller) thereof, may obtain the configuration change requests via receiving user input selections from a user. For example, a clinician may make selections from a user interface displayed by the external device. The user interface with available configuration changes may be received at the external device from a network, such as the Internet. Alternatively, the one or more processors of the external device may obtain the configuration change requests selected by the clinician by accessing the configuration changes from a memory device onboard the external device. The collection 112 of configuration change requests 114 may include parameters, settings, functions, algorithms, instructions, and/or the like for changing at least a portion of how the IMD operates. The configuration change requests 114 in the collection 112 may be related, such the execution of the requests 114 update different aspects of the IMD 102 to accomplish, in sum, a change of the IMD operating configuration.

At step 204, a set 128 of transaction credentials 130 is obtained. The transaction credentials 130 provide information about the programming package 108 to be conveyed to the IMD 102, such as identifying the source that generates the programming package 108. The transaction credentials 130 are used by the IMD 102 to verify that the programming package 108 is from an authentic source without being tampered or corrupted post-generation. In an embodiment, all of the following transaction credentials 130 are obtained. Alternatively, the transaction credentials 130 may not include at least one of the following examples. One transaction credential 130 is an expiration credential. The expiration credential includes a designated time in the future in which the programming package 108 (being constructed) will expire. Once the programming package 108 expires, the configuration change requests become moot.

Another transaction credential 130 is a target device credential that identifies the intended recipient of the programming package 108 being constructed. The target device is the device intended to execute the collection 112 of configuration change requests 114. The intended recipient may be specifically identified via including an identifier that is uniquely associated with one (and only one) particular device. In addition, or as an alternative, the intended recipient may be a device platform with which the programming package 108 is designed to be compatible. The device platform may include hardware and/or software.

A third transaction credential 130 is a role credential which provides a privilege level of a user that selected the configuration change requests 114. Role credential designates the level of privilege the programming requests are to be checked against. A given programming request can be initiated as a clinician-authorized configuration change for altering device operations behavior, or can be initiated as a remote care specific configuration change for device monitoring. The user that selects the requests can include the patient (in which the IMD 102 is implanted), a clinician that cares for the patient and is assigned to ensure the functionality of the IMD 102, or a third party that is neither the patient nor the patient's clinician. Each user may have to log in to a user interface prior to receiving access to viewing data generated by the IMD 102 and selecting the configuration change requests 114. The clinician has a greater privilege level than the patient, such that the clinician has enhanced permission to affect the functions of the IMD 102 than the patient. The role credential may also encompass other characteristics besides the user identity, such as the time that the user selected the configuration change requests 114 and/or whether the user is located near the patient or remote from the patient at the time that the user selected the configuration change requests 114.

In a non-limiting example, the IMD/external communication interface is based on Domain Information Model (DIM). Each command/request that is supported over this interface has a restricted level of access based on the access level at which the connection is made. The second external device 106 can be a remote patient application or a clinic programmer application. The clinic programmer application may be granted a higher permission level than the remote patient application such that some commands allowed for the clinical programmer application are not allowed if the connection is made with the remote patient application. The role credential may enable temporary use of other access roles within the context of the transaction. For example, via a role credential which sets the role to clinical programmer application, a user utilizing the remote patient application can execute a command that is typically only allowed for the clinical programmer application.

A fourth transaction credential 130 is a programming credential that identifies a current operating configuration utilized by the IMD 102, as understood by the external device that formulates the programming package 108. The current operating configuration includes the parameters, settings, algorithms, and the like that govern the behavior of the IMD 102 to monitor cardiac activity. In addition to, or as an alternative to, the current operating configuration, the programming credential may include a last programming timestamp that indicates a time at which the operating configuration of the IMD 102 was most recently updated, as understood by the external device that formulates the programming package 108.

Another transaction credential 130 may be a source credential which identifies a source device that generates the programming package 108, such as a specific external device (e.g., computer, server, program, or the like). The source credential optionally may identify a software version, firmware version, or the like, that is used to generate the programming package 108. Another transaction credential 130 is a hash credential which is an encrypted hash of the collection 112 of configuration change requests 114.

At step 206, a first hash of the collection 112 of configuration change requests 114 is generated. The first hash defines or represents the hash credential of the transaction credentials 130. The first hash is a cryptographic hash generated by applying a hash function to data. The data may be the configuration change requests 114 in the order of intended execution by the IMD 102. For example, the configuration change requests 114 may be concatenated in an array starting from first to last, without including non-request data such as strings identifying the start and/or end of the collection 112, and then the hash is generated by applying a hash function to the array. The first hash according to an embodiment is a SHA-256 hash, but may be another type of hash in another embodiment. Further examples of hash functions are described in (i) M. Singh and D. Garg, "Choosing Best Hashing Strategies and Hash Functions," 2009 IEEE International Advance Computing Conference, 2009, pp. 50-55, doi: 10.1109/IADCC.2009.4808979 and (ii) B. Preneel, "Cryptographic hash functions," Eur. Trans. Telecomm., 5: 431-448 (1994), https://doi.org/10.1002/ett.4460050406, and both articles are incorporated by reference herein.

At step 208, a signature 132 is generated using a key that is uniquely associated with the source that generates the programming package 108. For example, the source may be the first external device 104, so a key that is uniquely associated with the first external device 104 is used to generate the signature 132. In an embodiment, the signature 132 is a cryptographic encryption of one or more of the transaction credentials 130 in the set 128, generated using the key. The signature 132 may be referred to as a cryptographic signature. In a first example, the signature 132 is generated by encrypting the entire set 128, and only the set 128. In a second example, the signature 132 is an encryption of only a portion of the set 128, such as the hash credential only. In a third example, the signature 132 is an encryption of one or more of the transaction credentials 130 and one or more of the configuration change requests 114, optionally both the entire set 128 and the entire collection 112.

The key used to generate the signature 132 may be a private key that is a secret (e.g., not publicly known). The private key is only known to the associated device, which is the first external device 104 in this example. The signature 132 can only be decrypted using a public key that forms a key pair with the private key. The public key is also uniquely associated with the first external device 104, but is not a secret. For example, the public key of the key pair corresponding to the first external device 104 may be stored in the memory device 88 onboard the IMD 102. In another example, the key may be a symmetric key, such that the IMD 102 may use the same key to decrypt the signature 132.

At step 210, the programming package 108 is built by combining the collection 112 of configuration change requests 114, the set 128 of transaction credentials 130, and the signature 132. Optionally, the signature 132 may be grouped as one of the transaction credentials 130 in the set 128.

Optionally, if the programming package 108 is generated by one external device (e.g., device 104) and transmitted to the IMD 102 via an intervening external device (e.g., device 106), then the method may also include an authentication step for the hand-off of the package 108 between the external devices. For example, the first external device 104 may cryptographically sign the package 108, and then transmit the package 108 to the second external device 106. Upon receipt, the second external device 106 verifies the received package 108 and its signature to ensure the authenticity of the package 108 delivered between the entities. The signing of the package 108 may utilize the public key infrastructure of (e.g., public and private keys uniquely associated with) the devices 104 and 106. For example, the first external device 104 may cryptographically sign the entire package 108 using the public key of the second external device 106, and the second external device 106 may decrypt the received package 108 using the private key of the second external device 106. The private key of the second external device 106 is only known to the second external device 106, and only the private key is able to decrypt the message encrypted using the public key of the second external device 106, ensuring confidentiality of the transfer of the package 108.

At step 212, a communication session with the IMD 102 is established. The communication session is between the IMD 102 and one of the external devices. In an example, the external device that establishes the communication session is the second external device 106. For example, the first external device 104 may build the programming package 108 and then communicate the programming package 108 to the second external device 106. At a scheduled time of delivery, the second external device 106 establishes a communication session with the IMD 102. The communication session may be established via an RF handshake protocol that sets the rules for communications between the external device 106 and the IMD 102, including a frequency channel (e.g., communication link) on which to send and receive signals. Alternatively, the same external device that generates the programming package 108 may establish the communication session with the IMD 102.

At step 214, the programming package 108 is conveyed, via the established communication link, to the IMD 102. The programming package 108 may be wirelessly communicated via the communication circuit 120 of the second external device 106. Prior to executing the configuration change requests 114 of the programming package 108 that is received, the IMD 102 verifies the authenticity, validity, and integrity of the package 108.

Figure 5:
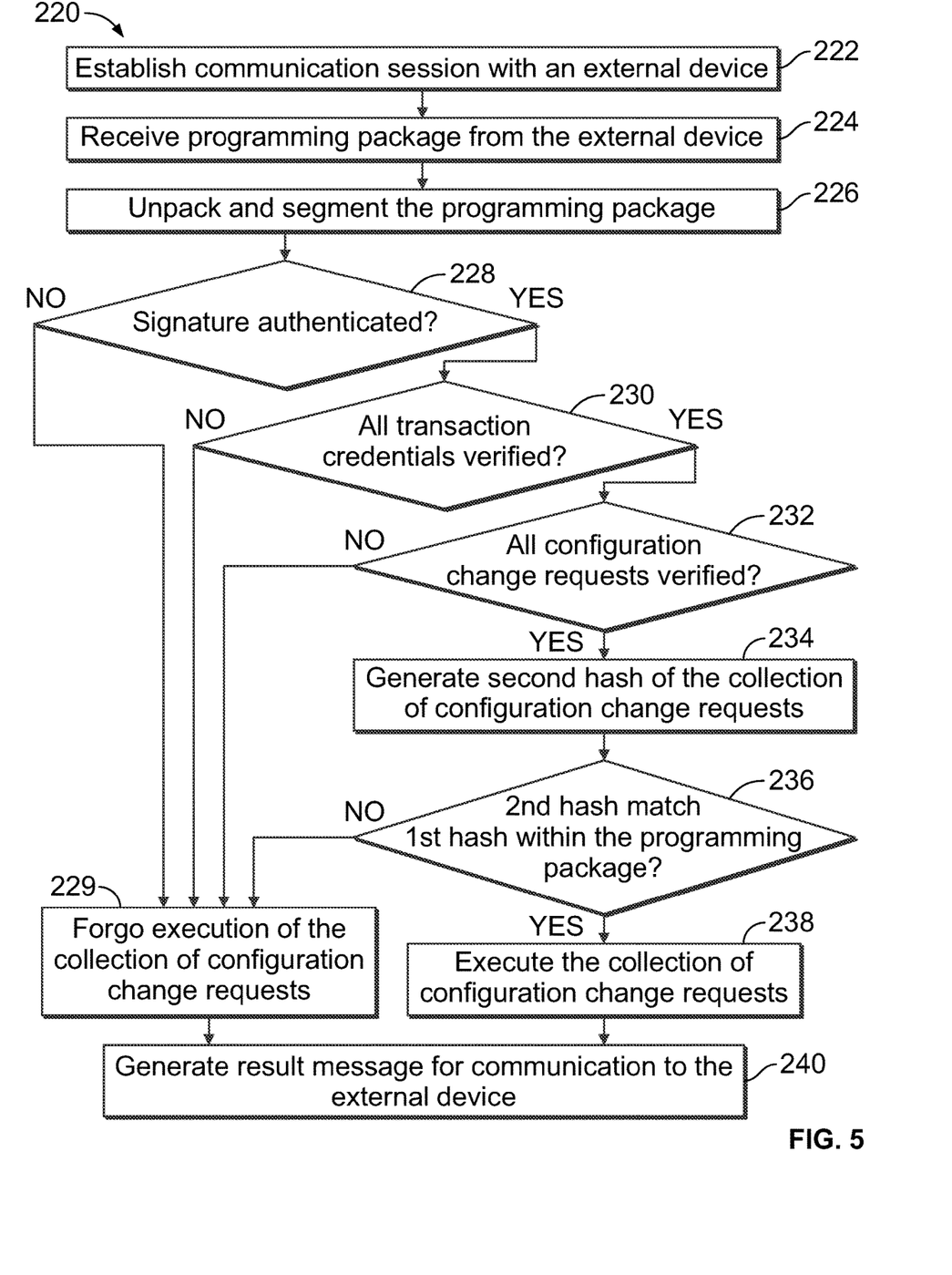
FIG. 5 is a flow chart of a method for securely analyzing a programming package prior to updating an operating configuration of an IMD.

FIG. 5 is a flow chart of a method 220 for securely analyzing a programming package prior to updating an operating configuration of an IMD. The method 220 shown in FIG. 5 may succeed or follow the method 200 in FIG. 4 to represent a method for providing secure, remote programming of an IMD. The method 220 is performed by the IMD 102. For example, at least some of the steps or operations of the method 220 are performed by one or more processors (e.g., the microprocessor 20) of the IMD 102.

At step 222, a communication session is established with an external device. The communication session may be the communication session described in operation 212 with reference to FIG. 4. At step 224, a programming package 108 is received from the external device during the communication session. The programming package 108 may be the programming package that is built in operation 210 and conveyed to the IMD in operation 214. In an embodiment, the IMD 102 receives the programming package 108 while the IMD 102 is disposed within the patient, such as within a subcutaneous and/or subdermal pocket of the patient anatomy. The programming package 108 may be wirelessly received via RF signals.

At step 226, the programming package 108 is unpacked and segmented into component parts. The component parts include at least a collection 112 of configuration change requests 114, a set 128 of transaction credentials 130, and a signature 132. In an embodiment, the non-signature parts of the programming package 108 are not encrypted. Alternatively, the programming package 108 may be encrypted for additional security, as described in more detail below.

At step 228, it is determined whether the signature 132 is authentic. The signature 132 indicates the source that generated the programming package 108. Validating the signature 132 proves the identity of the source, such that the alleged source identified in the transaction credentials 128 is confirmed. The signature 132 is validated by decrypting the signature 132 using either a copy of the same key (e.g., first key) that was used by the external device 104 in operation 208 of FIG. 4 to generate the signature 132, or a different key (e.g., second key).

In an embodiment, the external device 104 used a private key that is uniquely associated with the external device 104 to generate the signature 132, and the IMD 102 uses a public key, which forms a key pair with the private key, to decrypt the signature 132. The public key may be stored in the memory device 88 of the IMD 102, and accessed by the one or more processors (e.g., microprocessor 20) to decrypt the signature 132. By using a private-public key pair, the public key may be the only key that can decrypt the signature 132. Successful decryption of the signature 132 via using the public key uniquely associated with the external device 104 indicates that the external device 104 is the true source that generated the programming package 108. Keys associated with other devices would not be able to decrypt the signature 132.

Optionally, to determine that the decryption is successful, the one or more processors of the IMD 102 compare decrypted data to other, non-encrypted data in the programming package 108 to check for a match. The decrypted data is the output of the decryption of the signature 132 by using the public key stored in the IMD 102. The non-encrypted data that is compared to the decrypted data may include the set 128 of transaction credentials 130. For example, the signature 132 may be an encryption of one or more of the transaction credentials 130. If the decrypted data using the public key matches one or more of the transaction credentials 130 received in the set 128, then that confirms that the decryption is successful, the public key is the correct key, and therefore the external device 104 associated with the public key is the true source. In an alternative embodiment, the key that is used by the IMD 102 to decrypt the signature 132 may be a copy of the same key used by the source to generate the signature 132. Validating the source of the programming package 108 greatly reduces the likelihood of a malevolent actor impersonating an authorized source of the configuration change requests.

If the signature 132 is successfully authenticated as a valid source, then flow proceeds to step 230. If the signature 132 is not able to be authenticated, either through failure to decrypt the signature 132, the decrypted data not matching any of the non-encrypted data (e.g., transaction credentials 130), or the like, then flow proceeds directly to step 229. At step 229, the IMD 102 (e.g., the one or more processors thereof) forgo execution of the collection 112 of configuration change requests 114. The IMD 102 forgoes execution by not executing or implementing any of the configuration change requests 114. As a result, the operating configuration of the IMD 102 is not updated even though the programming package 108 is received and commands an update.

At step 230, after successful authentication of the signature 132, it is determined whether all of the transaction credentials 130 in the set 128 are verified. For example, the expiration credential is verified by determining that the programming package 108 is not expired (e.g., the expiration date has not yet passed). The target device credential may be verified by determining that the IMD 102 is the particular device that is identified as the intended recipient and/or has the specific device platform identified to execute the collection 112 of configuration change requests 114. In another example, the programming credential, which identifies the current operating configuration and/or the last programming timestamp, may be verified by confirming that the programming credential is correct. The one or more processors of the IMD 102 may access records from the onboard memory device 88 regarding the time of the preceding programming event and/or the current operating configuration, and then compare those records to the information in the programming credential. Verifying the programming credential is important because the configuration change requests 114 in the programming package 108 may instruct changes to a specific operating configuration that is believed to be the current configuration. If the specific operating configuration on which the requests 114 are based is not correct, such as if the IMD configuration has been updated again in the intermediate, then the requests 114 may not achieve the desired results when executed. The source credential may be verified in conjunction with the validation of the signature 132. For example, the source credential may identify the alleged source, and the validation of the signature 132 may authenticate the alleged source as the true source. The hash credential is inspected and verified at step 236. The role credential may be previously verified by requiring an authentication step of the user prior to selecting the requests 114 for the programming package 108. The role credential is used to verify the configuration change requests 114 at step 232.

If every (non-hash) transaction credential 130 in the set 128 is successfully verified, then flow proceeds to step 232. If one or more of the transaction credentials 130 are not verified, then flow proceeds to 229 to forgo execution of all configuration change requests 114.

At step 232, after successful verification of all non-hash transaction credentials 130, it is determined whether all of the configuration change requests 114 in the collection 112 are verified. The requests 114 may be verified one-by-one, like the transaction credentials 130, to determine if the syntax and/or arguments contained in the requests 114 are correct. The role credential is used to verify the configuration change requests 114 by determining whether each request 114 is within the privilege level associated with the role credential of the user. For example, if the role is of a patient, then very few, if any, configuration changes of the IMD 102 may be permitted. For clinicians, the privilege level allows the remote programming to make some configuration changes to the IMD 102. There may be a few critical functions of the IMD 102 that are not permitted to be modified through a remote programming operation, even when requested by a clinician. If any of the submitted requests 114 exceed the privilege level associated with the role credential, those requests 114 are not verified. Conversely, all of the requests 114 are verified if none of the requests 114 exceeds the privilege level of the role.

If every configuration change request 114 in the collection 112 is successfully verified, then flow proceeds to step 234. If one or more of the configuration change request 114 are not verified, then flow proceeds to 229 to forgo execution of all configuration change requests 114.

At step 234, a second hash of the collection 112 of configuration change requests 114 is generated. The first hash was generated by the source of the programming package 108 and included within the package 108 as one of the transaction credentials 130. The second hash is generated by the one or more processors of the IMD 102 based on the configuration change requests 114 received in the programming package 108. In an embodiment, the IMD 102 compiles the configuration change requests 114 in the order at which the requests 114 are received, and then generates a SHA-256 hash of the configuration change requests 114.

At step 236, it is determined whether the second hash, generated by the IMD 102, matches the first hash, generated by the source of the programming package 108. if the hashes match, then the one or more processors deduce that the collection 112 is correct and has not been tampered with or corrupted. For example, if a hacker attempted to tamper with a configuration change request 114 or add a new configuration change request to the collection 112, then the second hash would not match the first hash. The correspondence between hashes also ensures that the order of the configuration change requests 114 received by the IMD 102 matches the order constructed into the programming package 108. If the hashes do not match, then flow proceeds to 229 to forgo execution of the entire collection 112 of configuration change requests 114. If, on the other hand, the hashes match, then flow proceeds to step 238.

At step 238, the collection 112 of configuration change requests 114 is executed to update the operating configuration of the IMD 102. For example, the one or more processors of the IMD 102 execute or implement the requests 114 in order. All of the requests 114 are executed. It is noted that in order to reach step 238 and update the operating configuration, the one or more processors first authenticate or validate the signature, verify every transaction credential, including ensuring that the hashes match, and verify every configuration change request. All must pass inspection before updating the configuration of the IMD 102. If even one aspect fails inspection, then none of the configuration change requests 114 is executed. This all-or-nothing approach ensures that the IMD 102 does not perform an incomplete or partial update of the operating configuration, which could result in undesirable behavior.

At step 240, a result message is generated for communication to the external device that is the source of the programming package 108, such as the external device 104 in FIG. 3. The result message indicates whether or not the requests 114 in the programming package 108 have been executed to update the IMD 102. The result message can be generated and transmitted regardless of whether the remote programming operation was successful or not. The result message may include additional information, such as the timestamp at which the update occurred or an identification of which aspect failed the inspection. In response to receiving notification that the programming was unsuccessful, the source may generate another programming package 108 to retry the remote programming operation.

In an alternative embodiment, the confidentiality may be improved by including additional encryption and decryption operations. In one non-limiting example, each of the source external device and the IMD have a respective uniquely-associated public-private key pair. Optionally, after building the programming package at step 210 in FIG. 4, the source external device encrypts the programming package using the public key of the IMD. The encrypted data includes the signature 132, which itself is data encrypted using the private key of the source external device. Only the private key of the IMD can decrypt the programming package, which reduces the likelihood of tampering with the programming package prior to and during transmission to the IMD. The encrypted programming package is conveyed to the IMD as described above. Upon receipt, prior to unpacking the programming package at step 226 of FIG. 5, the IMD initially decrypts the programming package using the private key of the IMD.

CLOSING

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. The program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. An implantable medical device (IMD) comprising:
a housing configured to be implanted within a patient; and
one or more processors disposed within the housing and configured to:
receive, from an external device, a programming package comprising a collection of configuration change requests, transaction credentials, and a signature indicative of a source of the programming package, wherein one of the transaction credentials is a first hash of the collection of configuration change requests;
validate the external device as the source by decrypting the signature using a key that is uniquely associated with the external device;
verify the transaction credentials and the configuration change requests of the programming package;
generate a second hash of the collection of configuration change requests;
compare the second hash that is generated to the first hash that is received in the programming package; and
responsive to both (i) the second hash matching the first hash and (ii) the transaction credentials and the configuration change requests being verified, execute the collection of configuration change requests to update an operating configuration of the IMD.

2. The IMD of claim 1, wherein responsive to at least one of (i) the second hash not matching the first hash or (ii) at least one of the transaction credentials or the configuration change requests is not verified, the one or more processors are configured to forego execution of the collection of configuration change requests.

3. The IMD of claim 1, wherein the transaction credentials comprise an expiration credential that includes a designated time that the programming package expires, and the one or more processors are configured to verify the expiration credential of the transaction credentials by determining that the programming package is not expired.

4. The IMD of claim 1, wherein the transaction credentials comprise a target device credential that identifies one or both of a particular device or a device platform intended to execute the collection of configuration change requests, and the one or more processors are configured to verify the target device credential by determining that the IMD is the particular device or has the device platform.

5. The IMD of claim 1, wherein the transaction credentials comprise a role credential that provides a privilege level of a user that selected the collection of configuration change requests, and the one or more processors are configured to verify each of the configuration change requests by determining that each respective configuration change request does not exceed the privilege level associated with the role credential.

6. The IMD of claim 1, wherein the transaction credentials comprise a programming credential that identifies one or both of a current operating configuration of the IMD or a last programming timestamp indicating a most recent update of the operating configuration of the IMD, and the one or more processors are configured to verify the programming credential by confirming that the programming credential is correct.

7. The IMD of claim 1, wherein, responsive to execution of the collection of configuration change requests, the one or more processors are configured to generate a result message for communication to the external device, the result message indicating that the operating configuration of the IMD is updated.

8. The IMD of claim 1, wherein the key is a public key that is stored within a memory device of the IMD, and the signature in the programming package is generated by the external device using a private key that is uniquely associated with the external device and forms a key pair with the public key.

9. The IMD of claim 1, wherein the IMD has a communication modem that is configured to wirelessly receive the programming package while the IMD is subcutaneously disposed within the patient.

10. The IMD of claim 1, wherein the one or more processors are configured to validate the external device as the source of the programming package by determining that decrypted data of the signature matches one or more of the transaction credentials of the programming package.

11. The IMD of claim 1, wherein the one or more processors are configured to generate the second hash based on an order at which the configuration change requests of the programming package are received by the IMD.

12. A system comprising:
an implantable medical device (IMD) comprising a housing configured to be implanted within a patient and one or more processors disposed within the housing; and
one or more external devices, each of the one or more external devices comprising a controller and a communication circuit, the controller of at least one of the one or more external devices configured to:
obtain a collection of configuration change requests;
obtain a set of transaction credentials;
generate a first hash of the collection of configuration change requests, the first hash representing one of the transaction credentials in the set;
generate a signature by encrypting one or more of the transaction credentials in the set using a first key that is uniquely associated with an external device of the one or more external devices; and
build a programming package by combining the collection of configuration change requests, the set of transaction credentials, and the signature,
the communication circuit of at least one of the one or more external devices configured to wirelessly communicate the programming package to the IMD,
the one or more processors of the IMD configured to:
receive the programming package from the communication circuit of the one or more external devices;
validate the external device as a source of the programming package by decrypting the signature using either the first key or a second key that is uniquely associated with the external device, wherein the first key or the second key used to decrypt the signature is stored within a memory device of the IMD;
verify the transaction credentials and the configuration change requests of the programming package;
generate a second hash of the collection of configuration change requests; and
responsive to both (i) the second hash matching the first hash and (ii) the transaction credentials and the configuration change requests being verified, execute the collection of configuration change requests to update an operating configuration of the IMD.

13. The system of claim 12, wherein the first key is a private key associated with one of the one or more external devices, and the one or more processors of the IMD are configured to use the second key to decrypt the signature, the second key being a public key that forms a key pair with the private key.

14. The system of claim 12, wherein responsive to at least one of (i) the second hash not matching the first hash or (ii) at least one of the transaction credentials or the configuration change requests is not verified, the one or more processors of the IMD are configured to forego execution of the collection of configuration change requests.

15. The system of claim 12, wherein the one or more external devices comprise one or more of a clinician programmer device, a bedside monitor, a smartphone, a tablet computer, a laptop computer, a desktop computer, a server, or a wearable computer.

16. The system of claim 12, wherein the transaction credentials comprise the first hash and at least two of:
  - an expiration credential that includes a designated time that the programming package expires;
  - a target device credential that identifies one or both of a particular device or a device platform intended to execute the collection of configuration change requests;
  - a role credential that provides a privilege level of a user that selected the collection of configuration change requests; and
  - a programming credential that identifies one or both of a current parameter set of the IMD or a last programming timestamp indicating a most recent update of the operating configuration of the IMD.

17. The system of claim 12, wherein the communication circuit of the one or more external devices is configured to wirelessly communicate the programming package to the IMD while the IMD is subcutaneously implanted within the patient and the one or more external devices are outside of the patient.

18. A method comprising:
  - receiving, from an external device, a programming package at an implantable medical device (IMD) configured to be implanted within a patient, the programming package comprising a collection of configuration change requests, transaction credentials, and a signature indicative of a source of the programming package, wherein one of the transaction credentials is a first hash of the collection of configuration change requests;
  - validating, via one or more processors of the IMD, the external device as the source by decrypting the signature using a key that is uniquely associated with the external device and stored within a memory device of the IMD;
  - verifying the transaction credentials and the configuration change requests of the programming package;
  - generating a second hash of the collection of configuration change requests;
  - compare the second hash that is generated to the first hash that is received in the programming package; and
  - responsive to both (i) the second hash matching the first hash and (ii) the transaction credentials and the configuration change requests being verified, executing the collection of configuration change requests to update an operating configuration of the IMD.

19. The method of claim 18, wherein validating the external device as the source of the programming package comprises determining that decrypted data of the signature, using the key, matches one or more of the transaction credentials of the programming package.

20. The method of claim 18, wherein responsive to at least one of (i) the second hash not matching the first hash or (ii) at least one of the transaction credentials or the configuration change requests is not verified, the method comprises forgoing execution of the collection of configuration change requests.

* * * * *